(12) United States Patent
Mauvoisin

(10) Patent No.: US 8,621,903 B2
(45) Date of Patent: Jan. 7, 2014

(54) CONTINUOUS OR INSTRUMENTED INDENTATION DEVICE WITH CONVEX BEARING SURFACE AND USE THEREOF, PARTICULARLY FOR METAL SHEET INDENTATION

(75) Inventor: Gérard Mauvoisin, Chantepie (FR)

(73) Assignee: Universite de Rennes 1 (FR)

( * ) Notice: Subject to any disclaimer, the term of this patent is extended or adjusted under 35 U.S.C. 154(b) by 151 days.

(21) Appl. No.: 13/119,081

(22) PCT Filed: Sep. 15, 2009

(86) PCT No.: PCT/EP2009/061942
§ 371 (c)(1),
(2), (4) Date: Mar. 15, 2011

(87) PCT Pub. No.: WO2010/029179
PCT Pub. Date: Mar. 18, 2010

(65) Prior Publication Data
US 2011/0174036 A1      Jul. 21, 2011

(30) Foreign Application Priority Data

Sep. 15, 2008  (FR) ...................... 08 56192

(51) Int. Cl.
*B21C 51/00*        (2006.01)
(52) U.S. Cl.
USPC ............................................. 72/31.11; 72/81
(58) Field of Classification Search
USPC ............ 72/20.1, 75, 31.01–31.11; 73/20.01, 73/12.02, 12.03, 12.04, 12.05, 12.06, 73/12.07, 12.08, 12.09, 81, 85; 29/90.01
See application file for complete search history.

(56) References Cited

U.S. PATENT DOCUMENTS

| | | | |
|---|---|---|---|
| 3,805,598 A * | 4/1974 | Corcoran | 73/81 |
| 5,965,896 A | 10/1999 | Marton | |
| 6,718,820 B2 * | 4/2004 | Kwon et al. | 73/81 |
| 7,600,404 B2 * | 10/2009 | Prevey, III | 72/75 |
| 8,161,803 B2 * | 4/2012 | Oh et al. | 73/81 |

FOREIGN PATENT DOCUMENTS

| | | |
|---|---|---|
| DE | 4210599 A1 | 10/1993 |
| DE | 102005012365 A1 | 9/2006 |
| JP | 08-122239 A | 5/1996 |

OTHER PUBLICATIONS

International Search Report, PCT/EP2009/061942, dated Oct. 14, 2009.

* cited by examiner

*Primary Examiner* — Dana Ross
*Assistant Examiner* — Mohammad Nourbakhsh
(74) *Attorney, Agent, or Firm* — Lerner, David, Littenberg, Krumholz & Mentlik, LLP

(57) ABSTRACT

The invention relates to a continuous or instrumented indentation device for a material. The indentation device includes an indenter, a bearing means for the material to be indented, a means for moving the indenter and/or the bearing means for contacting the indenter with the material to be indented, and for pressing the indenter into the material, and a means for measuring the force and movement of the indenter when the indenter is pressed into the material. The bearing means includes a convex surface for receiving the material to be indented and is oriented towards the indenter so that the material is capable of bearing on the convex surface. The indenter may comprise a one-piece structure. The means for measuring the movement of the indenter when the indenter is pressed into the material includes at least three movement sensors angularly arranged at an equal distance about the indenter.

13 Claims, 6 Drawing Sheets

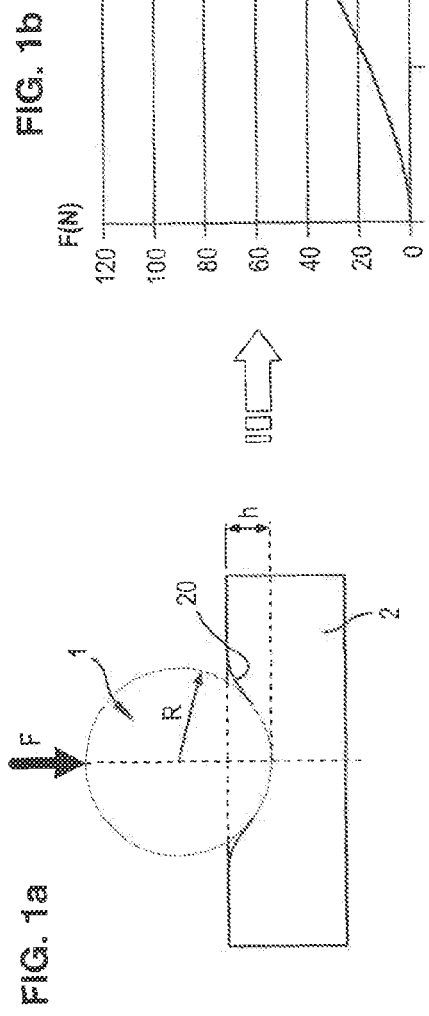
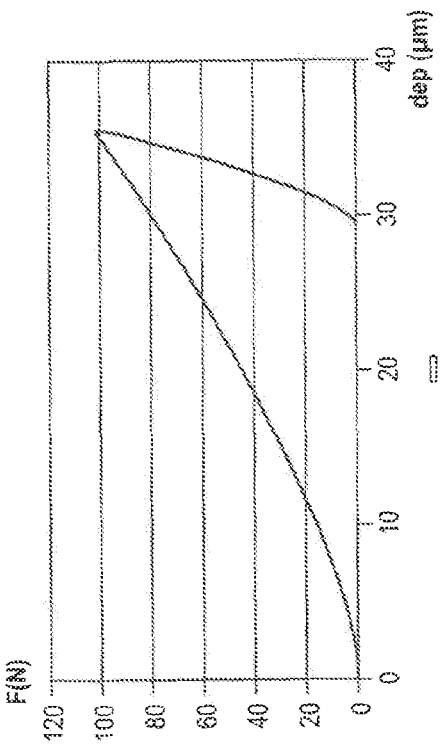
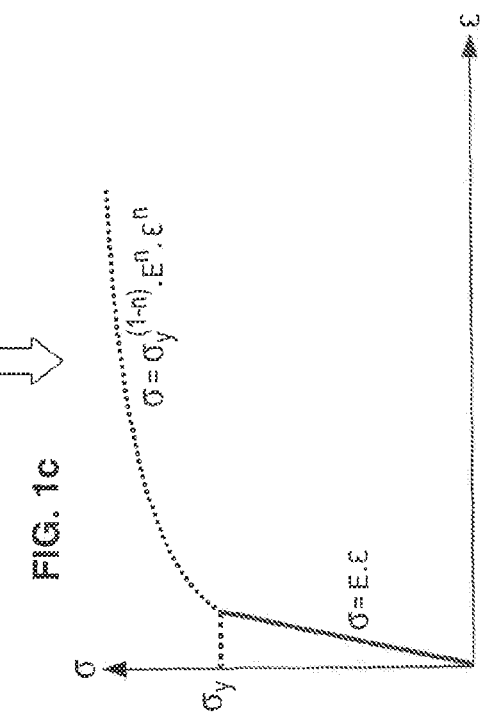
FIG. 1a
FIG. 1b
FIG. 1c

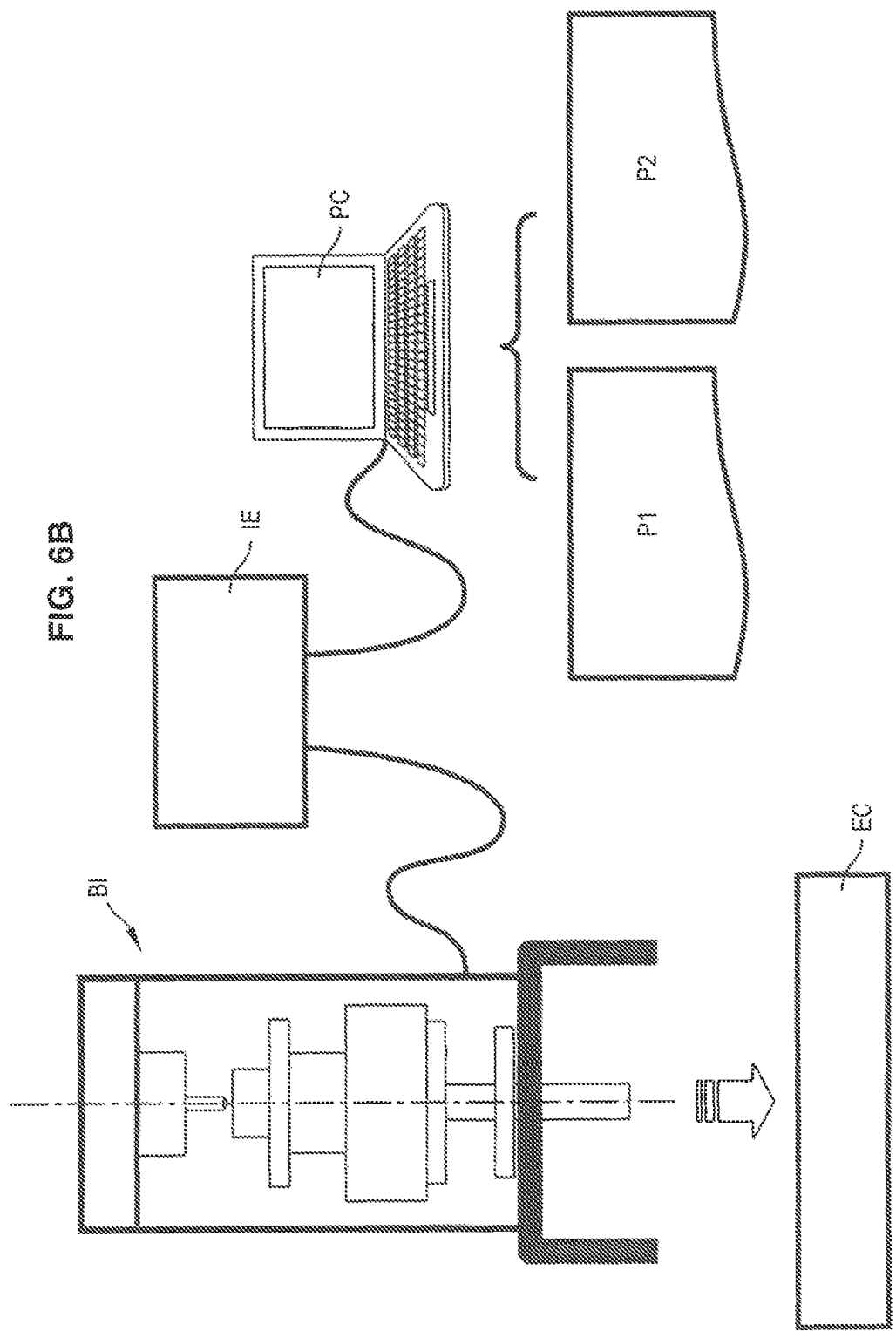

CONTINUOUS OR INSTRUMENTED INDENTATION DEVICE WITH CONVEX BEARING SURFACE AND USE THEREOF, PARTICULARLY FOR METAL SHEET INDENTATION

CROSS-REFERENCE TO RELATED APPLICATIONS

The present application is a national phase entry under 35U.S.C. §371 of International Application No. PCT/EP2009/061942, filed Sep. 15, 2009, published in French, which claims the benefit of French Patent Application No. 0856192, filed Sep. 15, 2008, the entire disclosures of which applications are incorporated herein by reference.

The present invention relates to a so-called "continuous" or "instrumented" indentation device. It also relates to the use of such a device for indentation of metal sheets, notably thin metal sheets, plates or sheet materials.

"Continuous" or "instrumented" indentation consists of measuring the force and the displacement undergone by an indentor during its sinking into a material to be tested.

This is what has been illustrated in appended FIG. 1a in which the tip (in the form of a ball of radius R) of an indentor is referenced as 1 and the material to be referenced as 2. The sinking of the tip 1 provides a deformation forming an imprint 20 at the surface of the material 2, of depth h.

The obtained indentation curve, an example of which is visible in FIG. 1b, illustrates the time-dependent change of the applied force F, versus the sinkage depth h of the indentor into the material. This curve, including a loading phase followed by an unloading phase, depends on many experimental parameters, as well as on the mechanical properties of the tested material.

Once the experimental parameters are controlled and set, the indentation curve is characteristic of the material (see FIG. 1c). It may be utilised for determining the parameters of the law of behaviour of the material, usually obtained by a tensile test on a test specimen of this material, which is destructive and requires a certain volume of material for making a specific and standardised specimen.

On the contrary, the indentation test is non-destructive, only requires a small volume of material and does not require any specific specimen.

The indentation test is a very local test, especially when it is used at a nanometric scale, in order to test very thin layers, and which does not prevent subsequent use of the sample on which the test has been conducted.

However, the lack of accuracy on the values of the measured sinkage depth makes it impossible to accurately determine the parameters of the materials, usually extracted from an indentation curve.

For example, the hardness H of the material is determined from the corresponding sinkage depth at the maximum applied load. The reduced modulus E* is also determined according to the Oliver and Pharr method, by utilising the slope of the curve F(h) at the beginning of the unloading.

Several methods also allow determination of the elastic limit of the material and of one or two work-hardening parameters. These methods are based on certain quantities extracted from the indentation curve, such as the curvature, the elastic energy, the plastic energy, the total energy, or the ratio of plastic energy to total energy. But all these quantities directly depend on the time dependent change of the sinkage depth h of the indentor during the test.

Thus, the parameters of the material can only be accurately inferred from an indentation curve if the sinkage depth is properly and accurately evaluated.

In FIGS. 2 and 3, structures of well known indentation devices are illustrated very schematically.

They comprise a rigid frame 4 which supports a plate 40 for receiving a material 2 to be tested.

In the embodiment of FIG. 2, the indentor 10 is attached vertically to the end of a support 100, which is made mobile also in the vertical direction by driving means 101. A displacement sensor 3 is attached between the upper portion of the frame 4 and of the support 100. It measures the displacement of the tip of the indentor 10 in the material.

In the alternative of FIG. 3, the indentor 10 is fixed and it is the support 40 of the material to be tested which is provided with driving means 400 in order to ensure its displacement in the vertical direction towards the indentor.

Regardless of the applied method, the first source of error in evaluating the sinkage depth is due to the fact that in practice, this sinkage depth which corresponds to the displacement of the lowest point of the indentor 10, is not directly measured but inferred from a measured displacement, in the best case, between the indentor 10 and the sample 2.

In order to overcome this difficulty, various more or less satisfactory solutions have been found.

Most solutions integrate into the measured value displacement related to the deformations of certain components of the frame or displacements due to geometrical defects of the test bench.

The second source of error is due to the use of commercial indentors, initially provided for determining hardness from the imprint left in the material, after applying and then removing a load. The indentors consist of a diamond or tungsten carbide tip, cut according to a geometry which depends on the type of hardness test, which is set and/or adhesively bonded in a cylindrical steel support, with an end which depends on the attachment method on the test bench.

The setting puts two surfaces into contact which never fit each other sufficiently well in order to avoid deformations at the interface between the tip and its support causing perturbations on the measurement of the sinkage depth.

These deformations are always rather small but never negligible considering the quantities which come into play during the indentation test.

As the geometrical characteristics of the surfaces in contact (including roughness) are unknown to the user, no modelling can be made for determining the deformations responsible for the closing-in movement of the tip towards its support during the test.

With both of these sources of error, it is therefore not possible to assimilate the measured displacement to the required sinkage depth.

Moreover, the indentation is generally practiced at a scale which depends on the available volume of material or on the thickness of the layers to be tested, in the case of coatings. This means that the load is adapted to the thickness of the part or of the coating to be studied.

Thus, in the case of metal sheets with a thickness of the order of 0.3 to 2 mm, the indentation should be practiced at a micrometric or even nanometric scale.

Now, metal materials have a microstructure consisting of multiple grains of different natures and of different sizes which make them a heterogeneous material at a microscopic scale.

On such materials, the indentation curves obtained with a low or very low load (less than 1 Newton) are not very reproducible, since they depend on the location where the test is practiced.

By applying a strong load (up to 100 or 200 N), the plastic deformation extends on a sufficiently large volume, with regard to the size of the grains, so as to be representative of the material. Thus, with indentation at a macroscopic scale it is possible to trace back the macroscopic behaviour of the material.

The difficulty encountered during macroscopic indentation of the metal sheets is related to the geometry of the surfaces. Indeed, it is practically not possible to produce metal sheet samples with a perfectly planar supporting surface.

Even rectification cannot smooth out flatness defects on thin metal sheets. Indeed, the magnetic plate used for attaching the metal sheet during rectification exerts a field of forces which deforms the metal sheet. After rectification, the rectified surface is planar as long as the metal sheet is not removed from its magnetic support.

Practically, when the metal sheet is removed from the magnetic plate, there may be flatness defects of several tens of micrometers (these defects are sometimes amplified during the manual polishing phase).

This is not very much, but the flexure which results from this may cause a parasitic displacement under the displacement sensor, which is of the order of the sinkage depths of the indentor during the indentation test.

As a result, the same indentation curve is not obtained depending on the location where the test is conducted on the sample.

The appended FIG. 4 illustrates this situation. The flatness defects of the list of materials 2 to be tested have been voluntarily exaggerated therein.

In this figure, two indentors 10 have been illustrated equipped with a support 50 for a sensor 5 for measuring sinkage depth.

Depending on whether the indentor (left portion of the figure) is located vertically above an area of the metal sheet properly bearing against its support 40, or at the vertical of a flatness defect (right portion of the figure—existence of play j under the metal sheet), the sinkage depth measurement recorded by the device will not be the same.

Problems of reproducibility of the results are observed. The obtained curves F(h) are not superposable as in the case of bulk materials.

This is what is illustrated in the enclosed FIG. 5, in which three non-superposable curves A, A', A" are obtained by testing the same sample at different locations.

The object of the present invention is to overcome these drawbacks.

In other words, it aims at proposing an indentation device which overrides flatness defects of the material, the testing of which is desired.

It also aims at proposing an indentation device which resumes the general structure of known indentation devices.

Thus, according to a first aspect of the invention, the latter relates to a device for so-called "continuous" or "instrumented" indentation of a material, which comprises:
   an indentor;
   means for supporting the material to be indented;
   means for displacing the indentor and/or supporting means, for putting said indentor in contact with said material, and for driving it into the latter;
   means for measuring the force and the displacement of the indentor during its sinking into the material,
   characterised by the fact that:

said supporting means comprise, in the extension of the longitudinal axis of said indentor, a convex surface for receiving said material, oriented towards the indentor, so that said material is capable of resting on this surface in a point-like or quasi point-like way;

said indentor is a one-piece indentor, i.e. it comprises an indentation tip which forms a single piece with the body of said indentor;

said means for measuring the displacement of the indentor during its sinking into the material comprise at least three displacement sensors angularly positioned in an equidistant way around said indentor.

By means of this device, it will be possible to obtain indentation curves on metal sheets, with the same reliability as on a bulk material. It allows use of the indentation curves, without any calibration, for quantitative evaluation of the properties of the materials.

Moreover, with this device it is possible to override all the "external" deformations for example inherent to the frame of the indentor.

According to other advantageous and non-limiting features of this device:
   said convex surface is the surface of a sphere or a sphere portion;
   said supporting means also comprise a plate on which rests said sphere or sphere portion;
   said plate includes means for blocking and/or attaching said sphere or sphere portion;
   said convex surface is in a single piece with a supporting plate;
   said indentor is in tungsten carbide or in any other material having great hardness;
   said sensors are of the contactless capacitive type;
   it comprises means capable of recording the distance measured by each of the sensors, as well as calculating the average of these three distances, this average being considered as being the sinkage depth value of the indentor into the material;
   said convex surface is formed by the tip of a second indentor which extends in the extension and in opposition to the first indentor;
   it assumes the shape of a pair of claws, each indentor being integral with a jaw of this pair of claws;
   only one of the indentors is provided with force measurement means;
   only one of the indentors is provided with displacement measurement means;
   both indentors are provided with means for measuring force and displacement.

The invention also relates to the use of a device according to one of the preceding features for the "continuous" or "instrumented" indentation of metal sheets, in particular thin metal sheets, plates or sheet materials.

Other features of the present invention will become apparent upon reading the detailed description which follows of certain embodiments. This description will be made with reference to the appended drawings wherein:

FIG. 6B is a diagram showing the installation into which the device according to the invention is integrated;

Figure 2:
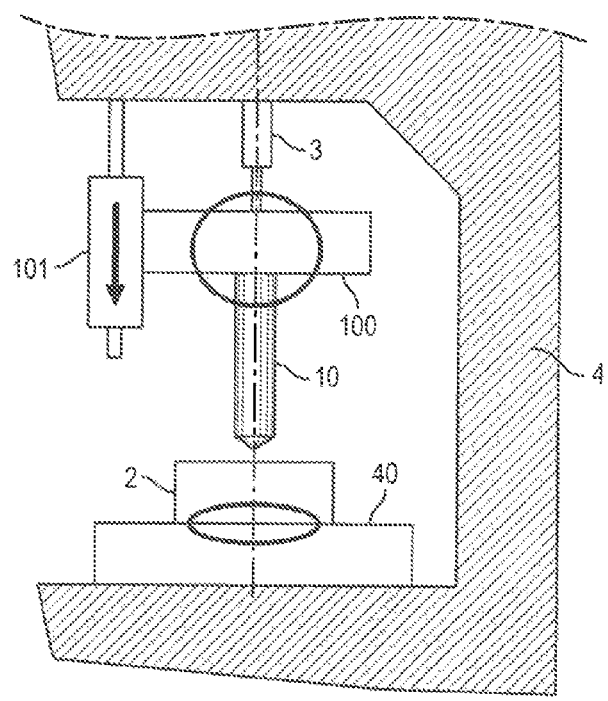
Figure 3:
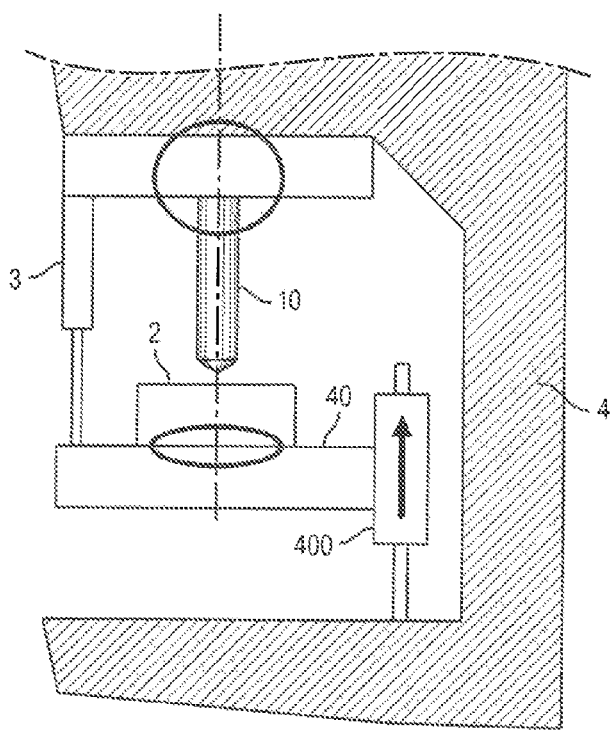
Figure 4:
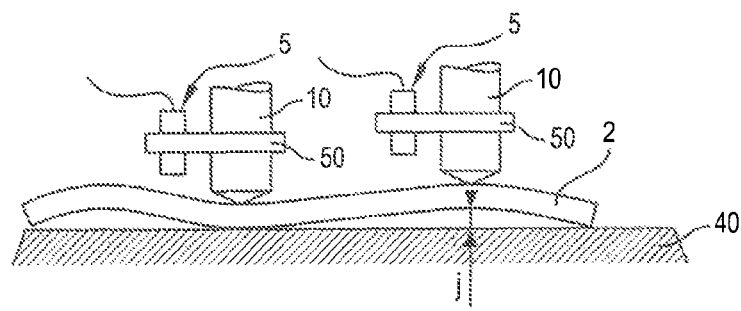
Figure 5:
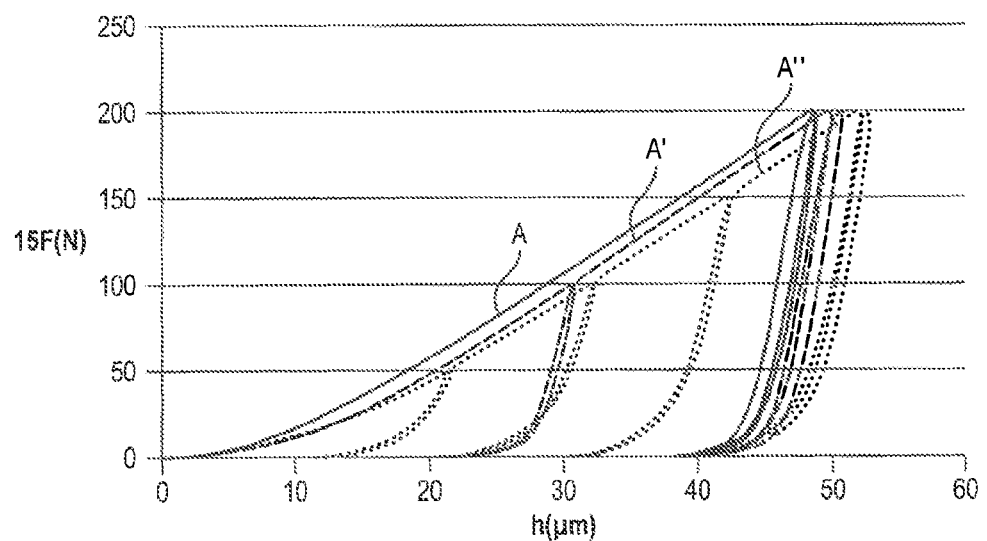
Figure 6A:
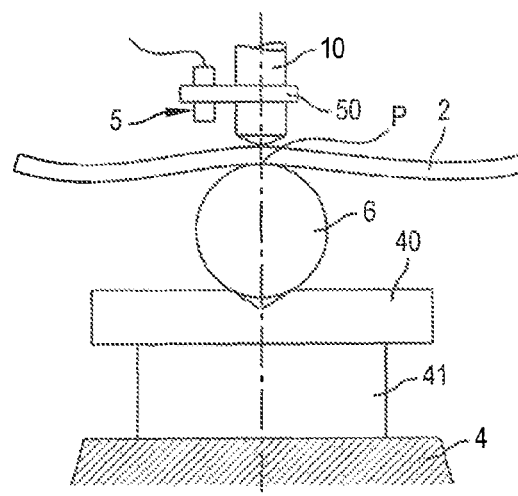
FIG. 6A is a very schematic view of a first embodiment of the device according to the invention.

Reference is now made to FIG. 6A in which a continuous indentation device according to the present invention is partly illustrated.

The latter was partially illustrated so as to only focus on the innovative aspects of this device.

An indentor 10 of a known type which extends vertically along an axis, as shown in FIG. 6A, is recognised therein.

In order to simplify the figure, the means allowing vertical displacement from top to bottom and vice versa of this indentor have not been illustrated.

The device is also provided with a plate 40 for receiving a material to be tested, this plate resting on force sensing means 41, themselves supported by the frame 4 of the device.

According to the present invention, the means for supporting the material 2 to be tested comprise, in the extension of the longitudinal axis of the indentor 10, a convex surface for receiving the material 2, oriented towards the indentor.

In this case, this convex surface is the surface of a sphere 6 which is positioned on the plate 40. For this purpose, a bore was made at the surface of this plate 40 ensuring annular linear contact between the sphere and the plate intended for immobilising the sphere 6.

In an embodiment not shown, the plate 40 may be provided with means for attaching said sphere.

This sphere is preferably in a hard material which only deforms elastically during the test.

Of course, the diameter of this sphere should be sufficient so as to hold the material sample to be tested in equilibrium therein. This more generally means that the radius of curvature of the convex surface should be less than that of the material 2, in the supporting region on this surface.

And it is understood that when the sphere is centred on the vertical axis of the indentor 10, the vertical force of the indentor on the material 2 causes, as a reaction, a vertical force of the sphere on this material, at right angles to the contact point.

Thus, flexure of the material 2 is avoided during the test.

In embodiments not shown, the sphere 6 may be replaced with a sphere portion or with any other component which has a convex contact surface with the material to be tested, so that the supporting area of this material on this support is point-like or quasi point-like.

In FIG. 6A, means are also illustrated for measuring the sinkage depth of the indentor into the material 2.

These means comprise a support 50 integral with the indentor 10 and the feelers 5 attached to this support 50.

Figure 7:
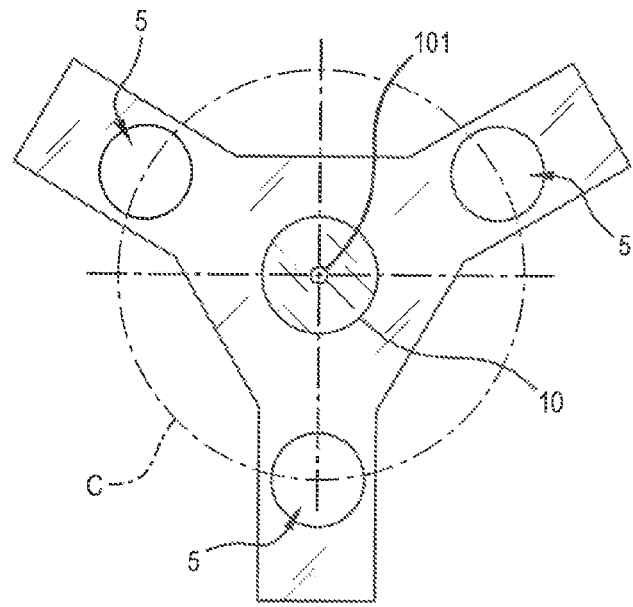
FIG. 7 is a schematic view from below, of an indentor which forms an integral part of the device according to the invention, and of three sensors (or feelers) with which it is equipped

These feelers or sensors are particularly visible in FIG. 7.

They are three or more in number, positioned along a fictitious circle C centred on the axis XX' of the indentor 10, angularly equidistant from each other and at an equal distance from the axis of the indentor. In the configuration with three sensors of FIG. 7, the latter form the apices of an equilateral triangle at the centre of which the indentor is found.

Preferably, these are contactless sensors of the capacitive type, i.e. capable of measuring, via suitable means, notably computer means, a potentiometric value depending on the distance between the sensors and the targeted material.

Computer means, not illustrated in FIG. 6A, are provided for transforming this value into a distance.

The fact that three angularly equidistant sensors are used here allows compensation for possible distance deviations read by either one or the other.

In order to take this variation into account, the computer means are also capable of calculating the average of these three measurements and of considering this average as equal to the sinkage depth value of the indentor into the material.

In FIG. 7, the tip 101 of the indentor 10 is also visible.

The latter is of the one-piece type, machined in the bulk of a tungsten carbide part. In other words, the tip 101 is of a single piece with the indentor 10.

An installation integrating the device according to the invention is very schematically illustrated in FIG. 6B. A conventional continuous indentation bench and additional pieces of equipment which it receives (plate 40, sphere 6, etc.) are designated as BI and EC respectively, for the application of the present invention.

This bench is connected to a PC computer, via an electronic interface for acquiring measurements conducted by the bench.

P1 and P2 designate software packages loaded into the computer, adapted for processing the acquired data.

The carrying out of an indentation test is performed by first taking into account the parameters of the indention test (such as the name of the application, the test velocity, the acquisition rate, the radius of the indentation tip, the maximum force which will be applied, the number of steps, the number of cycles at the end of loading).

The test is then conducted.

A software package or several associated software packages then assume several parallel tasks, i.e.:
control of the vertical displacement plate;
simultaneous acquisition of the axial force and of the three vertical displacement values;
display of the time-dependent change of the force versus time;
display of the time-dependent change of the force versus the sinkage depth of the indentor.

Finally, the software package records the data in a file.

These data may be utilised in a spreadsheet, by means of a specific software package or by an inverse analysis procedure.

Figure 8:
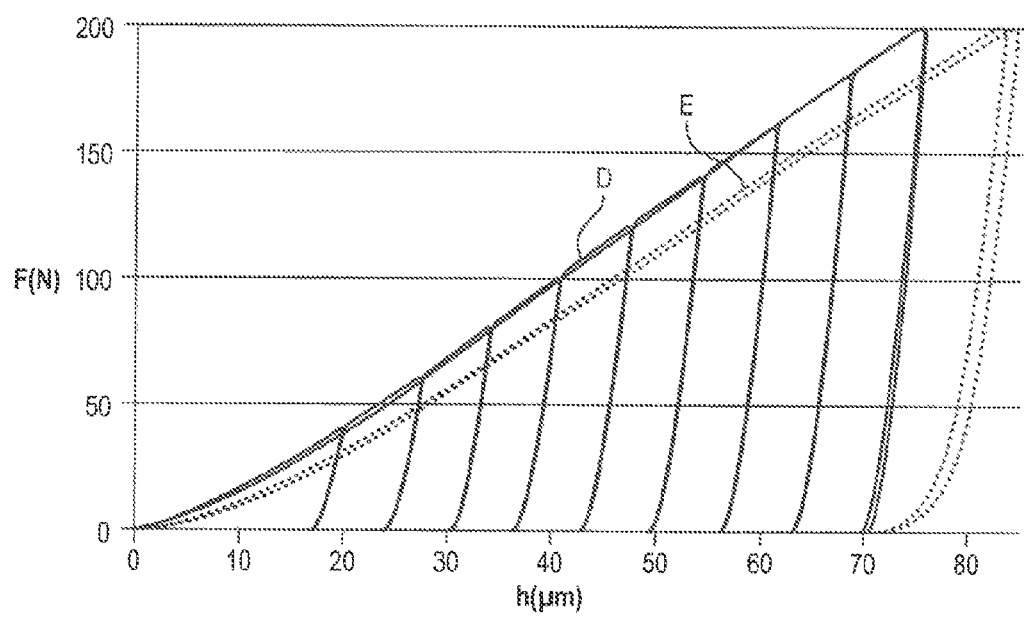
FIG. 8 shows a set of curves giving the value of the sinkage depth of an indentor versus the applied load, by using a device according to the invention.

In FIG. 8, the indentation curves obtained with the device according to the invention on the one hand (curves D) and with a device without any spherical support (curve E) are illustrated.

The curves D are much better superposed than the curves E, which shows that the device according to the invention allows the application of reproducible tests.

Moreover, the curves D have larger rigidity than the curves E. Indeed, in the configuration with a spherical support, the measured displacement is not perturbed by flexure of the metal sheet under the indentor. Finally, it is observed that regardless of the type of support, the residual plastic displacement at the end of the test is the same. This reinforces the idea according to which the deflection induced by flexure which is added to the sinkage depth in the absence of a spherical support, is elastic.

It is by means of the combination of the features according to the invention that such results are obtained, the device giving the possibility of overriding any parasitic deformation, i.e. extraneous to the material to be tested.

Figure 9:
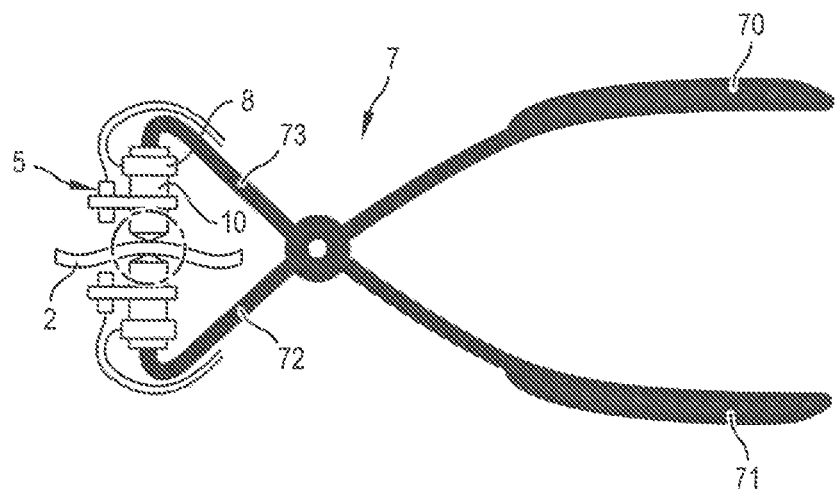
FIG. 9 is a front view of an alternative embodiment of the device.

In FIG. 9, a different embodiment of the indentation device is visible.

The latter assumes the form of a pair of claws 7 provided with handles 70 and 71 as well as with two associated jaws 72 and 73.

With these jaws 72 and 73 are associated two indentation devices according to the invention positioned facing each other, so that the tip 101 of one indentor 10 forms the convex surface for receiving the material and vice versa.

Figure 10:
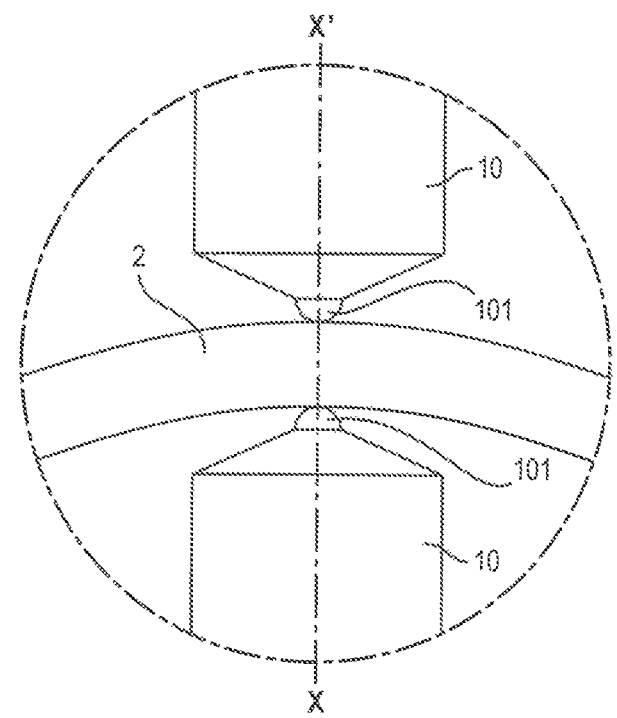
FIG. 10 is an enlarged view of the portion of FIG. 9 marked by a circle.

This situation is particularly visible in FIG. 10, in which the presence of both indentors 10 positioned along the same axis XX' is noted, the tip 101 of each of them forming a supporting surface opposite to the other.

This claw is therefore equipped with two indentation devices in opposition, each consisting of a one-piece indentor, of three capacitive sensors positioned at 120°, around and equidistant from the indentor axis, and with a force sensor.

This claw may be provided with a single force sensor located on the upper jaw or on the lower jaw. A configuration with two force sensors is most particularly justified when the metal sheet to be tested is sufficiently heavy for initiating indentation under its own weight.

Both indentors may either have the same geometry or not, since data acquisition is accomplished separately for the upper and lower sensors.

In the case when the lower indentor, which plays the role of a convex support, has the same curvature as the upper indentor, the claw produces a double indentation which is perfectly symmetrical when the tested material is perfectly homogeneous over its thickness.

In the case when both indentors have strictly the same geometry, and when the tested material is perfectly homogeneous, a single set of three displacement sensors, attached on the upper indentor is sufficient for properly carrying out the measurement since the device has a symmetrical structure.

However, if the tested material has a different mechanical behaviour on each of the upper and lower faces, or if the geometry of both indentors is slightly different, it is necessary to place two indentation devices as shown in FIG. 9 in order to carry out a correct measurement, i.e. with displacement sensors associated with each indentor. This configuration, with perfectly identical indentor geometries, will actually be able to allow detection of a possible mechanical behaviour difference between the upper face and the lower face of the studied metal sheet.

It is clear that the device of the present invention finds an application for the indentation of thin metal sheets. However, it applies to indentation of materials regardless of their thickness and their shape. This device is also suitable for indentation of materials consisting of layers of different nature.

Finally, the claw described above is particularly practical for carrying out indentation tests in situ.

The invention claimed is:

1. A device for continuous or instrumented indentation of a material, comprising:
   an indentor;
   means for supporting the material to be indented;
   means for displacing at least one of the indentor or the means for supporting the material, for putting said indentor in contact with said material and driving the material into the indentor; and
   means for measuring the force and the displacement of the indentor while the indentor is pressed into the material, wherein:
   (a) said means for supporting the material comprises a convex surface along a longitudinal axis of said indentor for receiving said material, the convex surface being oriented towards the indentor so that said material is capable of resting on the convex surface in a point-like or quasi point-like manner;
   (b) said means for supporting the material is free of other means for retaining the material in place;
   (c) said indentor is a one-piece indentor and comprises an indentation tip which is formed as a single piece with a body of said indentor; and
   (d) said means for measuring the displacement of the indentor while the indentor is pressed into the material comprises at least three displacement sensors angularly positioned equidistant from one another around said indentor, and positioned along a fictitious circle centred on the longitudinal axis of the indentor.

2. The device according to claim 1, wherein said convex surface is a surface of a sphere or of a sphere portion.

3. The device according to claim 2, wherein the means for supporting the material further comprises a plate on which the sphere or sphere portion rests.

4. The device according to claim 3, wherein the plate includes means for at least one of blocking or attaching said sphere or sphere portion.

5. The device according to claim 1, wherein the convex surface is formed as a single piece with a supporting plate.

6. The device according to claim 1, wherein said indentor comprises tungsten carbide.

7. The device according to claim 1, wherein the displacement sensors are contactless capacitive type sensors.

8. The device according to claim 1, further comprising means for recording a distance measured by each of the displacement sensors, and for calculating the average of the three measured distances, the average being considered as the sinkage depth value of the indentor in the material.

9. The device according to claim 1, further comprising a second indentor, wherein the convex surface is formed by a tip of the second indentor which extends in along the longitudinal axis in opposition to the first indentor.

10. The device according to claim 9, wherein the device is the form of a pair of claws, each indentor being integral with a jaw of the pair of claws.

11. The device according to claim 9, wherein only one of the indentors is provided with force measurement means.

12. The device according to claim 9, wherein only one of the indentors is provided with displacement measurement means.

13. The device according to claim 9, wherein both indentors are provided with force and displacement measurement means.

* * * * *